(12) United States Patent
Andersen et al.

(10) Patent No.: US 7,578,203 B2
(45) Date of Patent: Aug. 25, 2009

(54) SYSTEM FOR SAND DETECTION AT CONSTRICTIONS OR FLOW OBSTACLES IN A PIPE OR SIMILAR

(75) Inventors: Morten Ivar Andersen, Rádal (NO); Morten Brandt, Bønes (NO)

(73) Assignee: Roxar Flow Measurement AS, Bergen (NO)

( * ) Notice: Subject to any disclaimer, the term of this patent is extended or adjusted under 35 U.S.C. 154(b) by 180 days.

(21) Appl. No.: 11/628,539

(22) PCT Filed: Jun. 1, 2005

(86) PCT No.: PCT/NO2005/000179

§ 371 (c)(1), (2), (4) Date: Dec. 5, 2006

(87) PCT Pub. No.: WO2005/121770

PCT Pub. Date: Dec. 22, 2005

(65) Prior Publication Data

US 2008/0028838 A1 Feb. 7, 2008

(30) Foreign Application Priority Data

Jun. 7, 2004 (NO) .................................. 20042353

(51) Int. Cl.
G01F 1/66 (2006.01)
G01N 15/06 (2006.01)
(52) U.S. Cl. ................... 73/861.21; 73/61.75
(58) Field of Classification Search ................ 73/61.43, 73/61.73, 61.75, 861.18, 861.21, 861.23
See application file for complete search history.

(56) References Cited

U.S. PATENT DOCUMENTS

| 3,816,773 A | * | 6/1974 | Baldwin et al. | 310/319 |
| 3,841,144 A | * | 10/1974 | Baldwin | 73/61.75 |
| 3,906,780 A | | 9/1975 | Baldwin | |
| 3,939,709 A | * | 2/1976 | Echtler | 73/861.73 |
| 4,135,395 A | * | 1/1979 | Sullivan et al. | 73/861.21 |
| 4,448,062 A | * | 5/1984 | Peterson et al. | 73/86 |
| 4,607,254 A | * | 8/1986 | Carlson | 340/606 |
| 4,674,337 A | * | 6/1987 | Jonas | 73/861.73 |

(Continued)

FOREIGN PATENT DOCUMENTS

EP 0 254 882 2/1988

(Continued)

OTHER PUBLICATIONS

International Search Report for PCT/NO2005/000179 mailed Aug. 8, 2005.
Norwegian Search Report for 20042353 dated Jan. 13, 2005.
International Preliminary Report on Patentability for PCT/NO2005/000179 completed Oct. 5, 2006.

*Primary Examiner*—John Fitzgerald
(74) *Attorney, Agent, or Firm*—Nixon & Vanderhye P.C.

(57) ABSTRACT

This invention relates to a system for measuring solid particles, e.g. sand, in a fluid flow in a pipe, comprising at least one acoustic sensor for registering acoustic signals generated from collisions between particles and a surface. The pipe comprises a constriction through which the fluid flow passes, and that at least one of said acoustic sensors are positioned in relation to said constriction, and on a surface facing toward the flow so as to receive acoustic signals resulting from collisions between particles and the surface.

15 Claims, 2 Drawing Sheets

U.S. PATENT DOCUMENTS

Figure 1A:
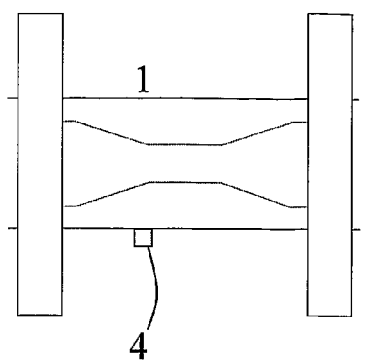

| | | | |
|---|---|---|---|
| 4,856,344 A * | 8/1989 | Hunt | 73/861.04 |
| 5,083,452 A * | 1/1992 | Hope | 73/61.49 |
| 5,257,530 A * | 11/1993 | Beattie et al. | 73/61.75 |
| 5,311,781 A * | 5/1994 | Gates | 73/861.25 |
| 5,571,974 A * | 11/1996 | Nauful | 73/861.27 |
| 5,681,986 A * | 10/1997 | Merk et al. | 73/61.75 |
| 5,747,671 A | 5/1998 | Hirota et al. | |
| 6,698,297 B2 * | 3/2004 | Gysling | 73/861.63 |
| 2004/0000197 A1 | 1/2004 | Gysling | |
| 2004/0007059 A1 | 1/2004 | Tudor | |

FOREIGN PATENT DOCUMENTS

| | | |
|---|---|---|
| EP | 0 769 695 | 4/1997 |
| GB | 2 396 011 | 6/2004 |
| NO | 166379 | 6/1989 |
| NO | 20015184 | 11/2002 |
| WO | 89/05974 | 6/1989 |
| WO | 2004/027350 | 4/2004 |

* cited by examiner

SYSTEM FOR SAND DETECTION AT CONSTRICTIONS OR FLOW OBSTACLES IN A PIPE OR SIMILAR

This application is the US national phase of international application PCT/NO2005/000179 filed 1 Jun. 2005, which designated the U.S. and claims benefit of NO 2004 2353, filed 7 Jun. 2004, the entire contents of each of which are hereby incorporated by reference.

The present invention generally relates to a system, and use for a system, for passive acoustic detection of sand/solid/particles, wherein the sensor(s) are positioned at constrictions or other forms of flow obstacles in a fluid transporting pipe, e.g. given by the mechanical design of some types of flow measuring devices.

Passive acoustic measuring systems are well established and known to be robust technology for detection of sand in oil, gas and multiphase fluid flows. Sensors "listen" to the fluid transporting pipeline of interest and obtain information by analyzing the amount of acoustic noise in the ultra sound region. A continuous measuring and monitoring of possible sand production in an oil well system makes it possible to optimize the production rate for individual wells, and give the operator important information for continuous evaluation of erosion in pipes and valves, as well as on intrusive process equipment. Reliable sand detection is therefore of great importance, both from economical and a security points of view.

Sound propagates good through metal. Acoustic sensors are therefore often mounted on the outside of pipes, with acoustic coupling to the pipe wall. This way direct exposure to the process and fluids is avoided, simplifying inspection and maintenance considerably.

The sensors in today's passive acoustic measuring systems are usually mounted by a knee (bend) in the pipeline. Here the fluid flow changes direction and the sensors pick up acoustic noise generated when sand or particles collide against or scrubs along the inside of the pipe wall because of momentum. Such an invention is e.g. described in Norwegian patent application No 1997 4904. The present invention utilizes the same physical principles—but includes detection at constrictions or other forms of flow obstacles in the fluid transporting pipes, e.g. given by the mechanical shape of some types of flow measuring devices. This may be realized by an alternative outer mounting of sensors corresponding to sensors being commercially available at the present, or better: by integrating one or more acoustic sensors/sensing elements inside the goods I or by a constriction/flow obstacle in "optimal" position relative to the sand impact.

Acoustic noise from sand colliding with the inside of a bens or construction detail in a pipeline will always be combined with a background of noise generated by the fluid flow itself, with contributions within the same frequency band. Therefore sand detection is based on relative measurements, and the system is calibrated or adjusted against the relevant flow conditions and rates. Under ordinary production information concerning flow rate is obtained from external sources, often through a supervising control system. The velocity is given directly or derived from rates or valve positioned and process parameters.

Dependency of external velocity input has several obvious disadvantages: it give dependency of sources possibly outside ones control, it increases complexity, and local variations are not captured, e.g. pulsed or uneven "slug" flow. These conditions are all potential sources of error and uncertainty. In the worst case the velocity information is not available at all.

Norwegian patent application No 2001 5184 discloses an alternative solution, with a sensor configuration and a method for integrated calculation of sand velocity based on cross correlation. The method does however, have some weaknesses, i.e. demanding two sensors per pipeline, mounted with at certain distance between them; it assumes that the channels are sufficiently correlated, which is not always the case; and the time response will be limited and a source for uncertainty at varying processing conditions.

In passive acoustic sand detection on a suitable flow measuring device an immediate, robust and reliable measuring of local flow velocity will be directly available for sand calculations, the sand and velocity measurements also being performed simultaneously. The opens for a much better handling of difficult flow conditions, such as slugging. Unwanted influence on the noise image may be compensated for so that accuracy and reliability is improved. The object of the invention is therefore to provide an improved system for sand detection.

Based on the description above the present invention thus obtains this object by providing the implementation of an independent instrument for sand detection, independent of input from external systems under normal use, and with an improved performance under difficult flow conditions. Such a solution with integrated velocity measurement will be of special interest for installations at the sea bed, where velocity information often is unavailable for the individual pipe lines where acoustic sand detectors are installed. More precisely the invention is characterized as disclosed in the attached independent claim.

More specific, but not exclusive, the invention relates to particle detection on flow measuring devices of types such as venturi, v-cone, vortex as well as possible use of velocity information from a current flow measuring device on the particle measurements. Physical and possible measure integration of otherwise well known technology may provide clear advantages relative to existing solutions.

In sand detection on flow measuring devices based in the differential pressure principle a local reduction in the cross section will lead to a local increase in the velocity, and as the kinetic energy of the sand particles increases in proportion with the velocity squared the amplitude of the sand noise will be a fast increasing function of the flow velocity. This may contribute to increase the noise measurements from sand from the current noise background, and thus increase the robustness of the sand detection. Minimum rate for detection will on the same background potentially be reduces relative to a corresponding installation at a pipe bend, so that the operation range is increased.

Examples of other advantages of the invention compared to other solutions based on post mounting of passive acoustic sensors at an existing pipe bend:

- Opening for sand detection also in long straight reaches along the pipeline. (Available pipe bend may e.g. be excluded because of proximity to a noisy choke valve.
- Prepared for optimized sensor positioning and sensor mount, independent of local structures on the specific installation (e.g. pipe curvature, welded joints, surface structures and protection layers, wall thickness etc).
- Prepared for better and more enduring acoustic coupling by fitted mounting on plane, machined surfaces. The coupling may be made permanent easier, e.g. by adhesives or liquid coupling.

The present invention has several similarities with Norwegian Patent No 166379 (EP0390835) as both are based on sensing acoustic noise by a construction detail or mechanical device affecting the flow in the pipe, both also including particle detection. There are, however, essential differences:

The mentioned patent relates to a method for determination of flow parameters or noise conditions which arise from a turbulent multiphase flow. Acoustic sensing elements are placed in close relation to a construction detail generating turbulent and noisy conditions, e.g. on or in the close vicinity of a constriction valve. The noise image here is strongly affected by the flow situation, and information may be interpreted from the measured signals through e.g. statistical methods. Preferred embodiments will typically mean measuring at construction details which can produce strong turbulence with cavitations, e.g. at sharp edges.

The present invention is not limited to multi phase flows, and is not dependent on turbulent flow conditions and the resulting characteristic flow noise. On the contrary a configuration is sought which generates as low noise as possible, in order to provide more secure sand detection. The preferred embodiments therefore will include "soft" transitions, e.g. in the constriction inside a venturi. Embodiments with e.g. sharp edged orifice plates will function best at lower velocities, where the turbulence from flow noise is limited. The present invention and the patent appear to be related, but the underlying principles are very different—with contradicting considerations to be made.

The mentioned patent claims to be a method which also comprises the determining of velocity from the acoustic signal. In sand detection on a suitable flow measurer the present invention provides an integrated velocity measurement based on other principles, such as differential pressure over a related constriction or correlation calculations based on two sand detectors in different positions along the pipeline.

The mentioned patent is primarily aimed at other goals than particle detection, and is therefore not specially adapted for this. Constriction valves are e.g. a known source of disturbing noise in passive acoustic sand detection and thus sensors are usually mounted at a good distance from them. In order to avoid this disadvantage the sensors according to the present invention are positioned in connection to a surface facing against the flow, i.e. before the turbulence occurs in the flow. The mentioned patent thus refers to a solution aimed at solving a different problem than EP0390835 which therefore is unsuitable for obtaining the result aimed at with the present invention.

The invention will be described below with reference to the accompanying drawings, illustrating the invention by way of examples.

Figure 1B:
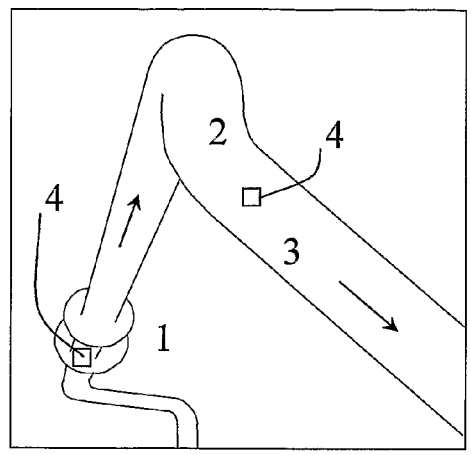
Figure 1C:
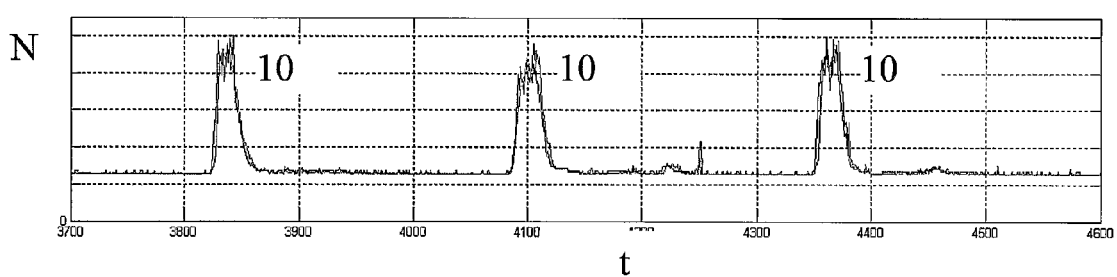

FIG. 1a-c illustrates positioning of sensors and a measured result obtained with such a configuration.

Figure 2:
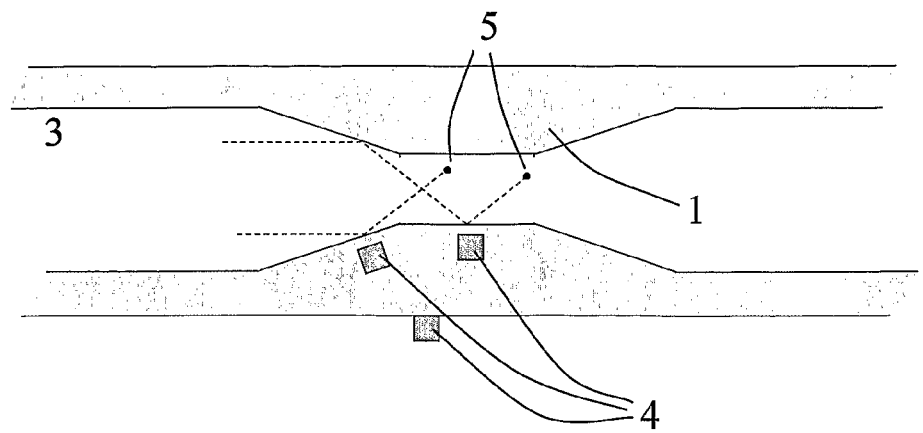
Figure 3:
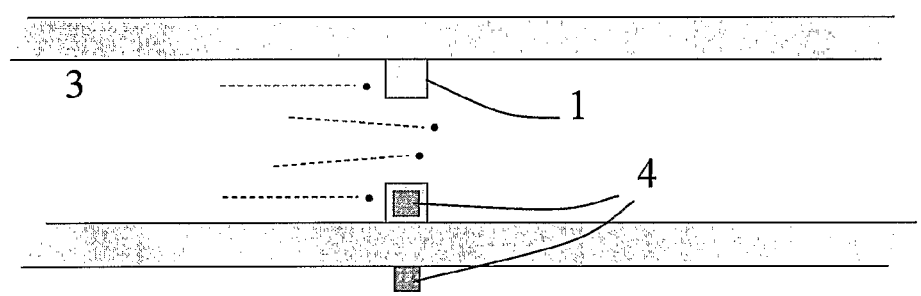
Figure 4:
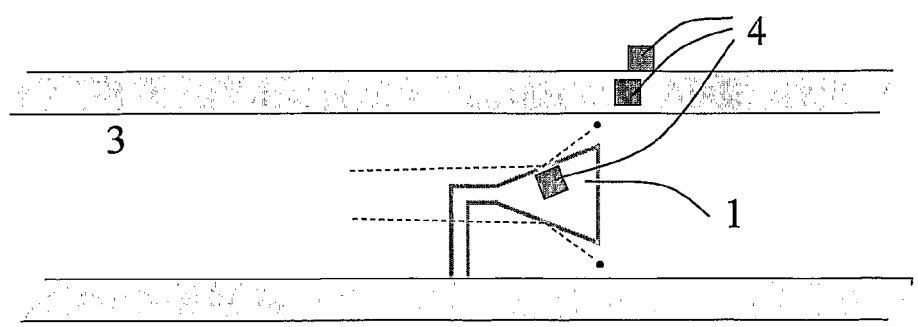

FIGS. 2-4 illustrates some alternative positions of acoustic sensors related to different types of flow obstacles.

FIG. 1a,b,c shows sketches and measured data from simple tests in a flow rig, where in FIG. 1a a passive acoustic sand sensor 4 was mounted outside a venturi type flow meter 1. The sensor is positioned close to the upstream part of the venturi. In FIG. 1b another sensor of the same type was mounted on a down flow pipe bend 2 in the same pipeline 3. In this example sand was injected into the pipe in three periods, which is seen as three marked peaks 10 in the noise measurements in FIG. 1c, in which the scales show a normalized nose level N as a function of time t The curves in FIG. 1c actually shows two lines from the two sensors in FIG. 1b, but normalized standard values N are sufficiently well correlated so that the results between the two different configurations are inseparable, and demonstrate that the concept behind the invention functions in practice. As described in the abovementioned Norwegian Patent Application 2001 5184 the velocity of the flow may be found by correlating the signals from the sensors in the configuration shown in FIG. 1b.

EXAMPLED EMBODIMENT OF THE INVENTION

In FIGS. 2, 3 and 4 different embodiments of the invention are shown having one or more acoustic sensors 4 are mounted both outside and/or inside the walls of a fluid transporting pipe 3 or pipe section/instrument for detecting collision of sand 5 against the pipe wall. Alternatively one or more acoustic sensors 4 are mounted directly on the constriction or flow limiter for increased sensitivity (e.g. directly on the cone in a v-cone type flow measuring device.) The important feature is that the sensor are placed in or acoustically coupled to positions that are chosen so as to receive as large a number of particle collisions as possible, thus obtaining a maximum sand noise level.

The sensor(s) are placed to detect sand or other hard particles 5 in the fluid flow with a passive acoustic measuring principle 4, by detection of acoustic noise generated when particles 5 collide with the constriction or flow limiter 1, or possibly an area of the pipe 3 closely downstream from this.

In preferred embodiments of the invention a flow measuring device of a type having a constriction or flow limiter over the pipe cross section may be provided with one or more acoustic sensors 4 for sand detection, and velocity information from the flow measuring device is used directly in the sand calculations. Electronics for calculating the sand rate will in the preferred embodiments be placed locally, physically close to the sensor elements. Thus an implementation may be realized of a independent instrument for passive acoustic sand measurements, independent of input from external systems under normal use. The invention supports passive acoustic sand measurements in long straight reaches of the pipeline. If the sensors are mounted on a device measuring flow velocity the calculation means may be shared so as to simplify the system and allow for the use of common parameters in the calculations.

FIG. 2 shows a simple sketch of the principle of a preferred embodiment of the invention, with sand detection on a venturi type 1 flow measuring device. The figure illustrates three alternative positions 4 for mounting the acoustic sensing element/sensors; two inside the steel wall at the constriction, and one on the outside of the constriction (e.g. mounting on an existing venturi).

It may also be possible to operate with several acoustic sensors on one and the same flow measuring device, both for redundancy in the measurements and for optimizing the detection with respect to the sensitivity for sand under varying processing conditions. In the shown case the first inner sensor from the upstream direction detects the first order collisions; the second inner sensor is positioned closely down stream from the constriction 1 and in this case detects second order collisions from particles that already have collided once with the wall, and the outer sensor receives both these signals. From this different parameters of the sand and flow may be found.

FIG. 3 illustrates in a similar way the use in an orifice plate type measuring device and it should be noted that the sensor is coupled to the left side of the plate so as to avoid the effects of turbulence. FIG. 4 illustrates the use on a v-cone measuring device wherein the sensor(s) 4 may be integrated inside the goods of the cone, and/or mounted in on the pipe wall for receiving sand having collided with the cone and reflected toward the wall.

The system according to the invention may be combined with a constriction constituting a part of a flow measuring device with means for utilizing measured rate/velocity in the particle movements. This may, as mentioned above, comprise a sensor positioned in another position at a constriction or a pipe bend, and calculation means for performing correlation measurements and particle detection. The calculation means used for this purpose as well as for sand noise analysis are per se well known in the art, e.g. referring to the patents and applications mentioned above, and will not be described in detail here, the scope of this invention being related to a system with the positioning of the sensors as referred to in the accompanying claims.

The invention claimed is:

1. A system to measure solid particles in a fluid flow in a pipe, the system comprising:
   at least one acoustic sensor for registering acoustic signals generated from collisions between the solid particles and a surface in a flow passage in the pipe through which the fluid flow passes, and
   a constriction in the flow passage through which the fluid flow passes, wherein
   the at least one acoustic sensor is positioned with respect to the pipe to be proximate a surface of the constriction facing the flow so as to receive acoustic signals resulting from collisions between particles and the surface, wherein said surface provides a soft transition for said fluid flow passing through the constriction to minimize turbulence resulting from the transition.

2. The system of claim 1 wherein the constriction is included in a flow measuring device detecting a flow rate of the fluid flow.

3. The system of claim 1 wherein the constriction has a venturi shape and the upstream surface is an outer surface of the flow passage forming a tapered surface portion the venturi.

4. The system of claim 1 wherein the constriction is included in a flow measuring device sensing a rate or velocity of the fluid flow.

5. The system of claim 1 further comprising a second acoustic sensor proximate a portion of the flow passage downstream of the at least one acoustic sensor detecting acoustic signals generated from collisions between particles in the fluid flow and the upstream surface in the flow passage.

6. A system to detect solid particles in a fluid flow in a flow passage of a pipe, the system comprising:
   a constriction in the flow passage of the pipe, wherein said constriction includes an upstream surface in the flow passage with respect to a flow direction of the fluid flow and the upstream surface gradually reducing a flow area in the flow passage at the constriction from a flow area in the flow passage upstream of the constriction and to a narrowest area in the flow passage in the constriction, and
   at least one vibration sensor for detecting vibration signals generated from collisions between particles in the fluid flow and the upstream surface in the flow passage.

7. The system of claim 6 wherein the at least one of said vibration sensors is positioned proximate to the upstream surface in the flow passage.

8. The system of claim 6 wherein the at least one vibration sensor comprises an acoustic sensor mounted on or in the pipe proximate to the upstream surface.

9. The system of claim 6 wherein the constriction is included in a flow measuring device detecting a flow rate of the fluid flow.

10. The system of claim 6 wherein the constriction has a venturi shape and the upstream surface is an outer surface of the flow passage forming a tapered surface portion the venturi.

11. The system of claim 6 wherein the constriction is included in a flow measuring device sensing a rate or velocity of the fluid flow.

12. The system of claim 6 further comprising a second acoustic sensor proximate a portion of the flow passage downstream of the at least one acoustic sensor detecting acoustic signals generated from collisions between particles in the fluid flow and the upstream surface in the flow passage.

13. A method to acoustically detect solid particles in a fluid flow in a flow passage of a conduit, the method comprising:
   passing the fluid flow through a constriction in the flow passage, wherein the constriction has an upstream surface gradually reducing a flow area of the flow passage in the constriction;
   minimizing creation of turbulence in the fluid flow passing through the constriction by the gradual reduction in flow area of the upstream surface of the constriction;
   generating vibrations in the conduit due to the solid particles impacting against the upstream surface;
   sensing the generated vibrations by at least one vibration sensor proximate to the upstream surface, and
   generating a signal based on the sensed generated vibrations which is indicative of a flow characteristic of the solid particles impacting the upstream surface.

14. The method of claim 13 wherein the step of generating vibrations includes generating acoustic vibrations and the step of sensing the generated vibrations includes sensing the acoustic vibrations.

15. The method of claim 13 further comprising sensing a rate or velocity of the fluid flow with a flow measuring device associated with the constriction.

* * * * *